(12) United States Patent
Miller (10) Patent No.: US 7,776,086 B2
(45) Date of Patent: Aug. 17, 2010

(54) ASPHERICAL CORNEAL IMPLANT

(75) Inventor: Troy Miller, Rancho Santa Margarita, CA (US)

(73) Assignee: ReVision Optics, Inc., Lake Forest, CA (US)

( * ) Notice: Subject to any disclaimer, the term of this patent is extended or adjusted under 35 U.S.C. 154(b) by 897 days.

(21) Appl. No.: 10/837,402

(22) Filed: Apr. 30, 2004

(65) Prior Publication Data

US 2005/0246015 A1     Nov. 3, 2005

(51) Int. Cl.
A61F 2/14        (2006.01)
(52) U.S. Cl. .................................. 623/5.11; 623/6.23
(58) Field of Classification Search ....... 623/5.11–5.16, 623/6.23, 6.24, 6.59
See application file for complete search history.

(56) References Cited

U.S. PATENT DOCUMENTS

| | | |
|---|---|---|
| 3,168,100 A | 2/1965 | Rich |
| 3,343,657 A | 9/1967 | Speshyock |
| 3,379,200 A | 4/1968 | Pennell |
| 3,482,906 A | 12/1969 | Volk |
| 3,743,337 A | 7/1973 | Crary |
| 3,770,113 A | 11/1973 | Thomas |
| 3,879,076 A | 4/1975 | Barnett |
| 3,950,315 A | 4/1976 | Cleaver |
| 4,030,480 A | 6/1977 | Meyer |
| 4,037,604 A | 7/1977 | Newkirk |
| 4,039,827 A | 8/1977 | Zdrok et al. |
| 4,071,272 A | 1/1978 | Drdlik |
| 4,157,718 A | 6/1979 | Baehr |
| 4,184,491 A | 1/1980 | McGannon |
| 4,194,814 A | 3/1980 | Fischer et al. |
| 4,238,524 A | 12/1980 | LaLiberte et al. |
| 4,257,521 A | 3/1981 | Poler |
| 4,268,133 A | 5/1981 | Fischer et al. |
| 4,326,306 A | 4/1982 | Poler |
| 4,392,569 A | 7/1983 | Shoup |

(Continued)

FOREIGN PATENT DOCUMENTS

DE        3208729 A1      9/1983

(Continued)

OTHER PUBLICATIONS

Cheng, et al.; "Predicting subjective judgment of best focus with objective image quality metrics"; Journal of Vision; vol. 4, pp. 310-321, 2004.

(Continued)

*Primary Examiner*—Paul Prebilic
(74) *Attorney, Agent, or Firm*—Shay Glenn LLP (57) ABSTRACT

A corneal implant having an aspheric surface for modifying the cornea curvature and altering the corneal refractive power. The corneal implant has a lens body formed of an optically clear bio-compatible material, preferably with an index of refraction substantially similar to that of human corneal tissue (1.376). The aspheric surface is comprised of a continuous aspheric surface from the apex of the implant to beveled surface. The beveled surface, positioned near the outer diameter of the implant, is used to reduce the thickness of the aspheric surface on the periphery of the lens to the outer diameter edge. The body of the implant has a diameter between about 2.0 mm and 7.0 mm and a thickness less than about 0.150 mm.

58 Claims, 4 Drawing Sheets

U.S. PATENT DOCUMENTS

| | | |
|---|---|---|
| 4,418,991 A | 12/1983 | Breger |
| 4,423,809 A | 1/1984 | Mazzocco |
| 4,428,746 A | 1/1984 | Mendez |
| 4,452,235 A | 6/1984 | Reynolds |
| 4,466,705 A | 8/1984 | Michelson |
| 4,490,860 A | 1/1985 | Rainin |
| 4,504,982 A * | 3/1985 | Burk .................... 623/6.23 |
| 4,521,210 A | 6/1985 | Wong |
| 4,525,044 A | 6/1985 | Bauman |
| 4,545,478 A | 10/1985 | Waldman |
| 4,554,115 A | 11/1985 | Neefe |
| 4,554,918 A | 11/1985 | White |
| 4,565,198 A * | 1/1986 | Koeniger .................... 606/166 |
| 4,580,882 A * | 4/1986 | Nuchman et al. ........... 351/161 |
| 4,586,929 A | 5/1986 | Binder |
| 4,604,087 A | 8/1986 | Joseph |
| 4,616,910 A | 10/1986 | Klein |
| 4,618,227 A | 10/1986 | Bayshore |
| 4,619,256 A | 10/1986 | Horn |
| 4,624,669 A | 11/1986 | Grendahl |
| 4,640,595 A | 2/1987 | Volk |
| 4,646,720 A | 3/1987 | Peyman et al. |
| 4,655,774 A | 4/1987 | Choyce |
| 4,662,370 A | 5/1987 | Hoffmann et al. |
| 4,663,358 A | 5/1987 | Hyon et al. |
| 4,671,276 A | 6/1987 | Reynolds |
| 4,676,792 A | 6/1987 | Praeger |
| 4,697,697 A | 10/1987 | Graham et al. |
| 4,702,244 A | 10/1987 | Mazzocco |
| 4,750,901 A | 6/1988 | Molteno |
| 4,762,496 A | 8/1988 | Maloney et al. |
| 4,766,895 A | 8/1988 | Reynolds |
| 4,806,382 A | 2/1989 | Goldberg et al. |
| 4,836,201 A | 6/1989 | Patton et al. |
| 4,840,175 A | 6/1989 | Peyman |
| 4,842,599 A * | 6/1989 | Bronstein .................. 623/5.15 |
| 4,844,242 A | 7/1989 | Chen et al. |
| 4,851,003 A | 7/1989 | Lindstrom |
| 4,860,885 A | 8/1989 | Kaufman et al. |
| 4,886,488 A | 12/1989 | White |
| 4,888,016 A | 12/1989 | Langerman |
| 4,897,981 A | 2/1990 | Beck |
| 4,919,130 A | 4/1990 | Stoy et al. |
| 4,934,363 A | 6/1990 | Smith et al. |
| 4,936,825 A | 6/1990 | Ungerleider |
| 4,946,436 A | 8/1990 | Smith |
| 4,955,903 A * | 9/1990 | Sulc et al. .................. 623/6.23 |
| 4,968,296 A | 11/1990 | Ritch et al. |
| 4,971,732 A | 11/1990 | Wichterle |
| 4,976,719 A | 12/1990 | Siepser |
| 5,019,084 A | 5/1991 | Aysta et al. |
| 5,019,098 A * | 5/1991 | Mercier .................... 623/6.24 |
| 5,041,081 A | 8/1991 | Odrich |
| 5,063,942 A | 11/1991 | Kilmer et al. |
| 5,071,276 A | 12/1991 | Nielsen et al. |
| 5,073,163 A | 12/1991 | Lippman |
| 5,092,837 A | 3/1992 | Ritch et al. |
| 5,098,444 A | 3/1992 | Feaster |
| 5,108,428 A | 4/1992 | Capecchi et al. |
| 5,112,350 A | 5/1992 | Civerchia et al. |
| 5,123,905 A | 6/1992 | Kelman |
| 5,123,921 A * | 6/1992 | Werblin et al. ............. 623/5.11 |
| 5,139,518 A | 8/1992 | White |
| 5,171,213 A | 12/1992 | Price, Jr. |
| 5,173,723 A | 12/1992 | Volk |
| 5,178,604 A | 1/1993 | Baerveldt et al. |
| 5,180,362 A | 1/1993 | Worst et al. |
| 5,181,053 A | 1/1993 | Brown |
| 5,188,125 A | 2/1993 | Kilmer et al. |
| 5,190,552 A | 3/1993 | Kelman |
| 5,192,317 A | 3/1993 | Kalb |
| 5,196,026 A | 3/1993 | Barrett |
| 5,211,660 A | 5/1993 | Grasso |
| 5,225,858 A | 7/1993 | Portney |
| 5,229,797 A | 7/1993 | Futhey et al. |
| 5,244,799 A | 9/1993 | Anderson |
| 5,258,042 A | 11/1993 | Mehta |
| 5,270,744 A | 12/1993 | Portney |
| 5,273,750 A | 12/1993 | Homiger et al. |
| 5,300,020 A | 4/1994 | L'Esperance, Jr. |
| 5,300,116 A | 4/1994 | Chirila et al. |
| 5,318,044 A | 6/1994 | Kilmer et al. |
| 5,318,047 A | 6/1994 | Davenport et al. |
| 5,336,261 A | 8/1994 | Barrett et al. |
| 5,338,291 A | 8/1994 | Speckman et al. |
| 5,346,464 A | 9/1994 | Camras |
| 5,370,607 A | 12/1994 | Memmen |
| 5,372,577 A | 12/1994 | Ungerleider |
| 5,385,582 A | 1/1995 | Ommaya |
| 5,391,201 A | 2/1995 | Barrett et al. |
| 5,397,300 A | 3/1995 | Baerveldt et al. |
| 5,405,384 A | 4/1995 | Silvestrini |
| 5,428,412 A | 6/1995 | Stoyan |
| 5,433,701 A | 7/1995 | Rubinstein |
| 5,454,796 A | 10/1995 | Krupin |
| 5,458,819 A | 10/1995 | Chirila et al. |
| 5,467,149 A | 11/1995 | Morrison et al. |
| 5,474,562 A | 12/1995 | Orchowski et al. |
| 5,476,445 A | 12/1995 | Baerveldt et al. |
| 5,493,350 A | 2/1996 | Seidner |
| 5,502,518 A | 3/1996 | Lieberman |
| 5,512,220 A | 4/1996 | Roffman et al. |
| 5,520,631 A | 5/1996 | Nordquist et al. |
| 5,521,656 A | 5/1996 | Portney |
| 5,530,491 A | 6/1996 | Baude et al. |
| 5,570,142 A | 10/1996 | Lieberman |
| 5,591,185 A | 1/1997 | Kilmer et al. |
| 5,598,234 A | 1/1997 | Blum et al. |
| 5,616,148 A | 4/1997 | Eagles et al. |
| 5,620,450 A | 4/1997 | Eagles et al. |
| 5,628,794 A | 5/1997 | Lindstrom |
| 5,630,810 A | 5/1997 | Machat |
| 5,634,943 A | 6/1997 | Villain et al. |
| 5,643,276 A | 7/1997 | Zaleski |
| 5,657,108 A | 8/1997 | Portney |
| 5,684,560 A | 11/1997 | Roffman et al. |
| 5,715,031 A | 2/1998 | Roffman et al. |
| 5,716,633 A | 2/1998 | Civerchia |
| 5,722,948 A | 3/1998 | Gross |
| 5,722,971 A | 3/1998 | Peyman |
| 5,752,928 A | 5/1998 | de Roulhac et al. |
| 5,766,181 A | 6/1998 | Chambers et al. |
| 5,772,667 A | 6/1998 | Blake |
| 5,785,674 A | 7/1998 | Mateen |
| 5,800,442 A | 9/1998 | Wolf et al. |
| 5,800,529 A | 9/1998 | Brauker et al. |
| 5,805,260 A | 9/1998 | Roffman et al. |
| 5,810,833 A | 9/1998 | Brady et al. |
| 5,817,115 A | 10/1998 | Nigam |
| 5,824,086 A | 10/1998 | Silvestrini |
| 5,847,802 A | 12/1998 | Menezes et al. |
| 5,855,604 A | 1/1999 | Lee |
| 5,860,984 A | 1/1999 | Chambers et al. |
| 5,872,613 A | 2/1999 | Blum et al. |
| 5,876,439 A | 3/1999 | Lee |
| 5,888,243 A | 3/1999 | Silverstrini |
| 5,913,898 A | 6/1999 | Feingold |
| 5,919,185 A | 7/1999 | Peyman |
| 5,928,245 A | 7/1999 | Wolf et al. |
| 5,929,968 A | 7/1999 | Cotie et al. |
| 5,929,969 A | 7/1999 | Roffman |
| 5,941,583 A | 8/1999 | Raimondi |
| 5,944,752 A | 8/1999 | Silvestrini |
| 5,945,498 A | 8/1999 | Hopken et al. |

| | | | | | | |
|---|---|---|---|---|---|---|
| 5,964,748 | A | 10/1999 | Peyman | 6,607,556 | B1 | 8/2003 | Nigam |
| 5,964,776 | A | 10/1999 | Peyman | 6,623,522 | B2 * | 9/2003 | Nigam ................... 623/5.13 |
| 5,976,150 | A | 11/1999 | Copeland | 6,626,941 | B2 | 9/2003 | Nigam |
| 6,007,510 | A | 12/1999 | Nigam | 6,629,979 | B1 | 10/2003 | Feingold et al. |
| 6,010,510 | A | 1/2000 | Brown et al. | 6,632,244 | B1 | 10/2003 | Nigam |
| 6,024,448 | A | 2/2000 | Wu et al. | 6,648,877 | B1 | 11/2003 | Juhasz et al. |
| 6,033,395 | A | 3/2000 | Peyman | 6,657,029 | B2 | 12/2003 | Vanderbilt |
| 6,050,999 | A | 4/2000 | Paraschac et al. | 6,666,887 | B1 | 12/2003 | Callahan et al. |
| 6,055,990 | A | 5/2000 | Thompson | 6,673,112 | B2 | 1/2004 | Nigam |
| 6,066,170 | A | 5/2000 | Lee | 6,709,103 | B1 | 3/2004 | Roffman et al. |
| 6,079,826 | A | 6/2000 | Appleton et al. | 6,712,848 | B1 | 3/2004 | Wolf et al. |
| 6,083,231 | A | 7/2000 | Van Noy et al. | 6,723,104 | B2 | 4/2004 | Ott |
| 6,086,202 | A | 7/2000 | Chateau et al. | 6,733,507 | B2 | 5/2004 | McNicholas et al. |
| 6,090,141 | A | 7/2000 | Lindstrom | 6,733,526 | B2 | 5/2004 | Paul et al. |
| 6,102,946 | A * | 8/2000 | Nigam ................... 623/5.15 | 6,808,262 | B2 * | 10/2004 | Chapoy et al. ............. 351/161 |
| 6,110,166 | A | 8/2000 | Juhasz et al. | 6,824,178 | B2 | 11/2004 | Nigam |
| 6,120,148 | A | 9/2000 | Fiala et al. | 6,875,232 | B2 | 4/2005 | Nigam |
| 6,129,733 | A | 10/2000 | Brady et al. | 6,879,402 | B2 * | 4/2005 | Kuchel ................... 356/513 |
| 6,142,969 | A | 11/2000 | Nigam | 6,881,197 | B1 | 4/2005 | Nigam |
| 6,143,001 | A | 11/2000 | Brown et al. | 6,893,461 | B2 | 5/2005 | Nigam |
| 6,159,241 | A | 12/2000 | Lee et al. | 7,128,351 | B2 | 10/2006 | Nigam |
| RE37,071 | E | 2/2001 | Gabrielian et al. | 2001/0051826 | A1 * | 12/2001 | Bogaert et al. ............. 623/6.23 |
| 6,183,513 | B1 | 2/2001 | Guenthner et al. | 2002/0101563 | A1 * | 8/2002 | Miyamura et al. ...... 351/160 R |
| 6,197,019 | B1 | 3/2001 | Peyman | 2003/0014042 | A1 | 1/2003 | Juhasz et al. |
| 6,197,057 | B1 | 3/2001 | Peyman et al. | 2003/0078487 | A1 | 4/2003 | Jeffries et al. |
| 6,197,058 | B1 * | 3/2001 | Portney ................... 623/6.34 | 2003/0088313 | A1 * | 5/2003 | Nigam ................... 623/5.13 |
| 6,203,538 | B1 | 3/2001 | Peyman | 2004/0049267 | A1 | 3/2004 | Nigam |
| 6,203,549 | B1 | 3/2001 | Waldock | 2005/0080485 | A1 | 4/2005 | Nigam |
| 6,206,919 | B1 | 3/2001 | Lee | 2005/0113844 | A1 | 5/2005 | Nigam |
| 6,210,005 | B1 | 4/2001 | Portney | 2005/0119738 | A1 | 6/2005 | Nigam |
| 6,214,015 | B1 | 4/2001 | Reich et al. | 2005/0143717 | A1 | 6/2005 | Peyman |
| 6,214,044 | B1 | 4/2001 | Silverstrini | 2005/0178394 | A1 | 8/2005 | Slade |
| 6,217,571 | B1 | 4/2001 | Peyman | 2005/0182350 | A1 | 8/2005 | Nigam |
| 6,221,067 | B1 | 4/2001 | Peyman | 2005/0246016 | A1 | 11/2005 | Miller et al. |
| 6,228,114 | B1 | 5/2001 | Lee | 2006/0116762 | A1 * | 6/2006 | Hong et al. ................. 623/5.16 |
| 6,248,111 | B1 | 6/2001 | Glick et al. | 2006/0212041 | A1 | 9/2006 | Nigam |
| 6,250,757 | B1 | 6/2001 | Roffman et al. | 2006/0235430 | A1 | 10/2006 | Le et al. |
| 6,251,114 | B1 | 6/2001 | Farmer et al. | 2007/0129797 | A1 | 6/2007 | Lang et al. |
| 6,264,648 | B1 | 7/2001 | Peyman | 2007/0203577 | A1 | 8/2007 | Dishler et al. |
| 6,267,768 | B1 | 7/2001 | Deacon et al. | 2007/0255401 | A1 | 11/2007 | Lang |
| 6,271,281 | B1 | 8/2001 | Liao et al. | 2007/0280994 | A1 | 12/2007 | Cunanan |
| 6,280,449 | B1 | 8/2001 | Blake | | | | |
| 6,280,470 | B1 | 8/2001 | Peyman | | | | |
| 6,283,595 | B1 | 9/2001 | Breger | | | | |
| 6,325,509 | B1 * | 12/2001 | Hodur et al. ............. 351/160 R | | | | |
| 6,361,560 | B1 * | 3/2002 | Nigam ................... 623/5.14 | | | | |

FOREIGN PATENT DOCUMENTS

| | | |
|---|---|---|
| EP | 0308077 | 3/1989 |
| EP | 0420549 A2 | 4/1991 |
| JP | 01-195853 | 8/1989 |
| JP | 02-211119 | 8/1990 |
| JP | 08-501009 | 2/1996 |
| WO | WO 96/26690 A1 | 9/1996 |
| WO | WO 98/08549 A1 | 3/1998 |
| WO | WO 98/48715 A1 | 11/1998 |
| WO | WO 99/17691 A1 | 4/1999 |
| WO | WO 99/21513 A1 | 5/1999 |
| WO | WO 99/30645 A2 | 6/1999 |
| WO | WO 00/38594 A1 | 7/2000 |
| WO | WO 03/041616 A1 | 5/2003 |
| WO | WO 03/061518 A2 | 7/2003 |
| WO | WO 03/101341 A2 | 12/2003 |

OTHER PUBLICATIONS

Marsack, et al.; "Metrics of optical quality derived from wave aberrations predict visual performance"; Journal of Vision; vol. 4; pp. 322-328; 2004.

Dishler, Jon et al.; U.S. Appl. No. 11/692,835 entitled "Insertion system for corneal implants," filed Mar. 28, 2007.

Lang, Alan et al.; U.S. Appl. No. 11/738,349 entitled "Biomechanical design of intracorneal inlays," filed Apr. 20, 2007.

Churms, P.W., "The Theory and Computation of Optical Modifications to the Cornea in Refractive Keratoplasty," American Journal of Optometry & Physiological Optics, 56:2, pp. 67-74, Feb. 1979.

Warsky, M.A. et al., "Predicting Refractive Alterations with Hydrogel Keratophakia," Investigative Opthalmology & Visual Science, vol. 26, pp. 240-243, Feb. 1985.

Liou, H. L. et al., "Anatomically accurate, finite model eye for optical modeling", Journal of the Optical Society of America, vol. 14, No. 8, Aug. 1997.

* cited by examiner

ASPHERICAL CORNEAL IMPLANT

TECHNICAL FIELD

The field of this invention relates to prosthetic implants designed to be implanted in the cornea. More particularly, the invention relates to a corneal implant having an aspheric surface for modifying the cornea curvature and altering the corneal refractive power.

BACKGROUND OF THE INVENTION

Normal vision occurs when light that passes through and is refracted by the cornea, the lens, and other portions of the eye, and converges at or near the retina. Myopia or near-sightedness occurs when the light converges at a point before it reaches the retina and, conversely, hyperopia or far-sightedness occurs when the light converges a point beyond the retina. Other abnormal conditions include astigmatism where the outer surface of the cornea is irregular in shape and effects the ability of light to be refracted by the cornea. In addition, in patients who are older, a condition called presbyopia occurs in which there is a diminished power of accommodation of the natural lens resulting from the loss of elasticity of the lens, typically becoming significant after the age of 45.

Corrections for these conditions through the use of implants within the human cornea have been suggested. Various designs for such implants include solid, ring shaped, and split-ring shaped, circular flexible body members and other types of ring-shaped devices that are adjustable. These implants are inserted within the body of the cornea for changing the shape of the cornea, thereby altering its refractive power.

Generally, the human cornea flattens away from the center. The reasons are not completely clear, though one known factor is that as the cornea flattens it reduces the spherical aberration. Therefore, I consider it desirable to reshape the cornea and maintain an aspheric surface that naturally occurs while correcting for refractive error. I believe there is a demonstrated need for a more effective corneal implant that has an aspheric surface that will correspond more naturally to the surface of the human eye to address the problems as previously discussed.

BRIEF SUMMARY OF THE INVENTION

The present invention is directed to prosthetic implants designed to be implanted in the cornea. More particularly, the invention relates to a corneal implant having an aspheric surface for modifying the cornea curvature and altering the corneal refractive power. The implant has a continuous aspheric surface extending from a center point or apex of the anterior surface of the lens body. This continuous aspheric surface preferably extends for a radius of at least 1 mm from the center or apex of the lens body. The continuous aspheric surface is continually aspheric along the surface and does not contain any portion of the aspherical surface that is spherical.

The lens body is preferably formed of an optically clear bio-compatible material. The bio-compatible material has an index of refraction substantially similar to that of human corneal tissue (1.376). Thus, in a preferred embodiment, the refractive index of the implant material should be in the range of 1.36-1.39. Having such a refractive index prevents optical aberrations due to edge effects at the cornea-implant interface.

The optically clear bio-compatible material is preferably made from a visually clear, permeable, microporous hydrogel with a water content greater than 40% up to approximately 90%. Other suitable bio-compatible materials, however, may be used.

The lens body has an anterior surface, a posterior surface, and an outer diameter edge. The anterior surface is generally convex in shape with a continuous aspheric surface. In one embodiment, the posterior surface is concave in shape with a posterior radii of curvature. However, the posterior surface may shaped differently, such as being substantially planar, having multiple radii of curvature, and other shapes as would be readily useful.

In a preferred embodiment, the lens body has a thickness less than about 0.150 mm, an outer diameter edge thickness of about 0.015 mm, and a diameter between about 2.0 mm and about 7.0 mm.

The implant may be formed with a beveled surface. The beveled surface assists in maintaining the required edge thickness while increasing lens strength. Preferably, the beveled surface has a convex shape that has a partially spherical or partially aspherical surface.

In one aspect of the invention, there is a method of implanting the various embodiments of the inventive corneal implant as described herein. The method includes the steps of (a) cutting away a portion of the outer surface of a cornea; (b) implanting a lens on the exposed surface of the cornea, the lens having a lens body formed of an optically clear, bio-compatible material, the lens body having an anterior surface and a posterior surface, and an outer diameter edge; the bio-compatible material having a refractive index ranging from 1.36-1.39, and the anterior surface being convex in shape with a continuous aspheric surface; and (c) replacing the portion of the cornea that was cut away.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

As used herein, the term "a" or "an" may mean one or more. As used herein in the claim(s), when used in conjunction with the word "comprising", the words "a" or "an" may mean one or more than one. As used herein, "another" may mean at least a second or more.

As used herein, the term "mm" means the unit of measurement in millimeters.

Most current surgical procedures are just coming of age in regards to aspheric surfacing. There is considerable published data on the anterior corneal surface asphericity. The common corneal shape is either a conic in certain sections or conicoids using three-dimensional data. The results are usually expressed in terms of asphericity Q, shape factor p or the eccentricity e. The mean values of the corneal surface are in the approximate range Q=−0.2 to −0.3. One thought is that the reason the human cornea flattens is to reduce spherical aberration.

When spherical aberration is present, non-paraxial rays do not intersect at the paraxial focus. By producing a spherical surface on the eye, the amount of asphericity is reduced that the cornea has and in turn, a spherical aberration is created. In most accounts the result will be a better near visual acuity because the center rays are still basically unaffected, but the intermediate and distance can loose some visual acuity.

To decrease the spherical aberration and also correct for visual disorders, one must look at the following. Maintain the natural aspheric surface that the cornea has, and flatten or steepen the cornea at the same time.

By doing the described, the central rays can be left as they are or increased (in the case of presbyopia) and at the same time flatten or decrease the radius from apex to the edge, bringing all rays within the paraxial focus. The actual radius is determined by what correction is needed to correct the visual disorder. All radius of curvature are dependent on the individual refraction of a patient.

Figure 1A:
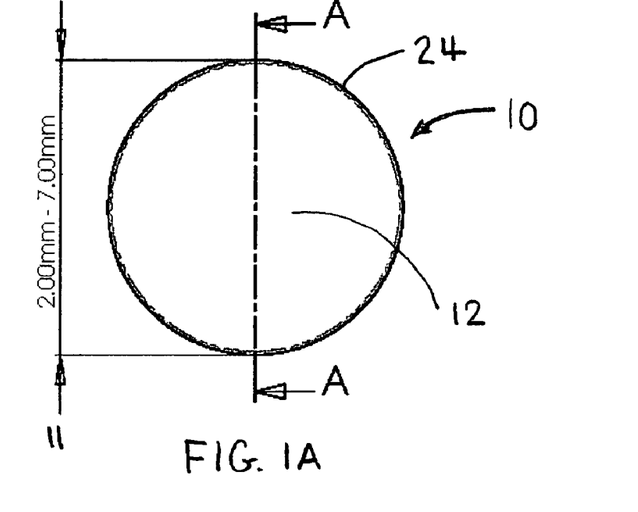
FIG. 1A is a top of an embodiment of the corneal implant.
Figure 1B:
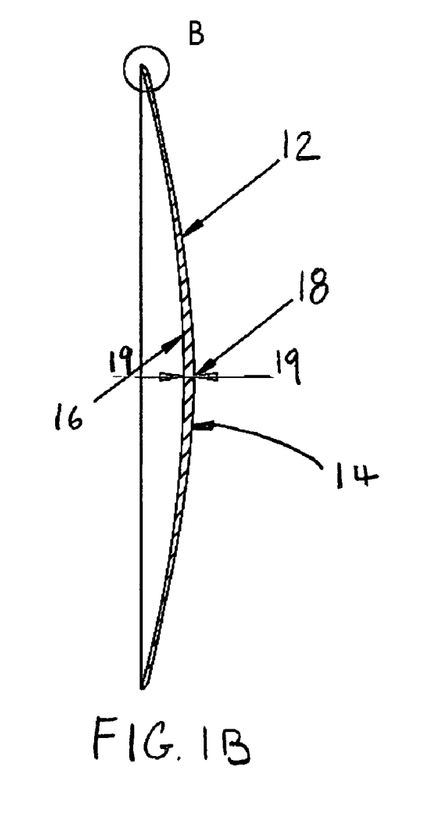
FIG. 1B is a 3-dimensional, cross-sectional view A-A of the implant of FIG. 1A.

Referring to FIG. 1A-1B, an embodiment of the aspherical corneal implant is shown. FIG. 1A is a top view of the implant. The implant 10 has a diameter (as shown by arrows 11-11) in the range of about 2.00 mm to 7.00 mm. The anterior surface 14 of the implant 10 has an aspheric surface 12 that is generally convex in shape. The aspheric surface 12 is comprised of a continuous aspheric surface from apex 18 to the transition zone 22. The transition zone 22 is the junction that begins the beveled surface 20. The beveled surface 20 is used to reduce the thickness of the aspheric surface 12 on the periphery of the lens to the outer diameter edge 24. Given that the implant 10 has a maximum useful diameter for implantation into the human cornea the implant without the beveled surface, would be too thick at the edges to properly seat the implant into the cornea. An edge thickness as specified prevents stacking and recruitment of keratocytes in the lens material so that keratocyte stacking and recruitment does not take place. This in turn eliminates unorganized collagen that forms undesirable scar tissue and infiltrates the lens, which tends to compromise the efficacy of the lens.

Referring now to FIG. 1B, a 3-dimensional, cross-sectional view of the implant 10 of FIG. 1A is shown. The implant 10 has an aspheric surface 12 from the apex 18 of the anterior surface of the lens to a transition zone 22. The radius of the aspheric surface 12 extends from the apex 18 outward towards the outer diameter edge 24. This radius is not less than 1.0 mm and the radius is not greater than the total radius to the beginning of the transition zone 22.

The implant 10 has a posterior surface 16 that is generally concave in shape. Where the implant is circular in shape, the apex 18 is also the center point of the lens. In one embodiment, the lens body has a thickness (as indicated by arrows 19-19) of less than about 0.150 mm. The center of the lens in most cases is the thickest part of the lens.

In a preferred embodiment, the posterior surface 16 is concave in shape with a posterior radii of curvature. However, the posterior surface 16 may shaped differently, such as being substantially flat or planar, having multiple radii of curvature, or utilizing other shapes as would be readily useful. In these other embodiments where a different shape posterior surface is utilized, than the thickness of the implant at its center may be greater than 0.150 mm. However, when using a concave shaped poster surface 16, preferably the thickness should be less than about 0.150 mm.

Figure 1C:
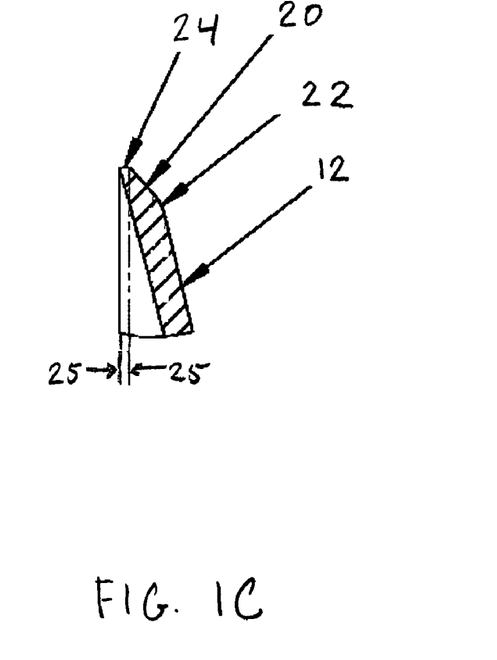
FIG. 1C is a 3-dimensional, cross-sectional view of the area B of FIG. 1B.

FIG. 1C is a close-up view of the area designated by the letter B in FIG. 1B. Preferably, the implant 10 has an outer diameter edge 24 that has substantially planar surface. The outer diameter edge 24 surface may also be spherical, or of other shapes that would be useful. Preferably, the outer diameter edge 24 has a thickness of about 0.015 mm. The thickness of the outer diameter edge is illustrated by arrows 25-25.

A beveled surface 20 transitions the anterior portion of the outer diameter edge 24 with the aspheric surface 12. In one embodiment, the shape of the surface of the beveled surface is substantially spherical with a radii of curvature, but in other embodiments may be substantially aspherical, substantially planar or other of useful shapes. Preferably, where the beveled surface 20 is spherical, the beveled has a single radii of curvature. The beveled surface 20 has a radius between about radius 1.5 mm-10.5 mm depending on the width of the implant. The beveled surface 20 and the aspheric surface 12 intersect at a junction 22. This junction 22 is referred herein, interchangeably, as the transition zone 22. The transition zone 22 provides a smooth transition from the beveled surface 20 to the aspheric surface 12. The transition zone 22 is preferably aspheric.

In one embodiment, the aspheric surface 12 comprises a continuous aspheric surface with a Q-value of less than zero, wherein Q is the surface asphericity and Q<0 represents a surface that flattens away from its vertex. The aspheric surface 12 may have a single Q-value or multiple Q-values for different zones on the surface of the implant, with each Q-value being less than zero. This can be expressed in terms of quantity p called the shape factor, which is related to Q by the equation p=1+Q or as eccentricity which is related to Q by the equation $Q=-e^2$.

Q is represented by the following equation—

$$h^2 + (1+Q)Z^2 - 2ZR = 0$$

where the Z axis is the optical axis,
where $h^2 = X^2 + Y^2$, and
where X, Y are distances perpendicular to optical axis,
where R is the vertex or apex radius of curvature.
Q is the surface asphericity, where
Q<−1 specifies a hyperboloid,
Q=−1 specifies a paraboloid, −1<Q<0 specifies an ellipsoid, with the Z-axis being the major axis, Q=0 specifies a sphere, Q>0 specifies an ellipsoid with the major axis in the X-Y plane.

Figure 3:
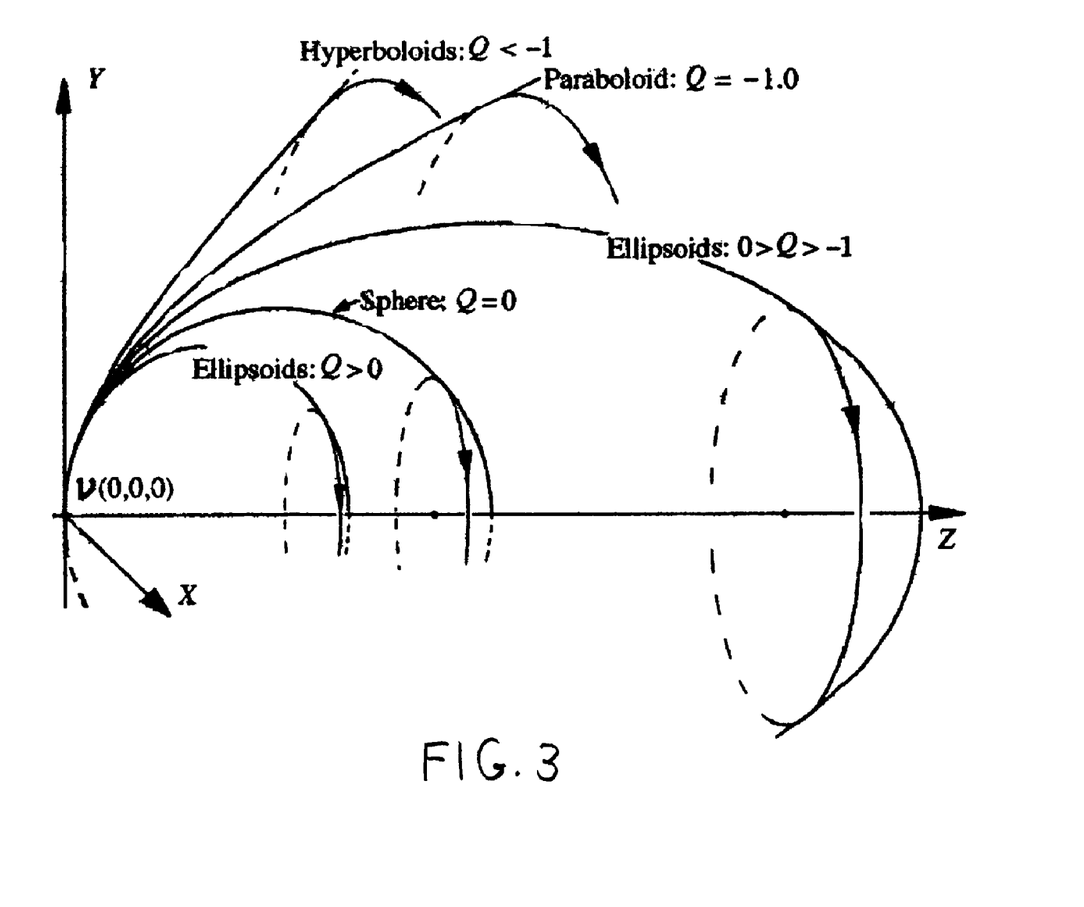
FIG. 3 is a diagram showing the effect of asphericity on the shape of a concoid.

Referring to FIG. 3, the effect of asphericity on the shape of a concoid is shown. All of the curves have the same apex radius of curvature. The figure shows an -X, -Y, -Z axis with the particular axis labeled respectively. The general Q value equation discussed above is diagramatically illustrated in the figure: Ellipsoids, Sphere, Hyperboloids, and Paraboloids.

By varying the Q value of the aspheric surface 12, the corneal implant 10 aids in the correction of presbyopia, hyperopia, myopia or the combination thereof, while maintaining an the actual corneal surface of the eye in an aspheric manner. The following Table 1 illustrates different Q values for different lens parameters. Table 1 is merely illustrative and should not be construed to limit the size and ranges of the various parameters shown.

TABLE 1

| Approximant Diopter Change | Posterior Radius | Anterior Apex Radius | Anterior End Radius | Anterior Semi-Diameter | Anterior Asphericity (Q) |
|---|---|---|---|---|---|
| 1.25 | 7.500 | 7.147 | 7.508 | 3.820 | −0.118 |
| 1.75 | 7.500 | 7.081 | 7.508 | 3.820 | −0.138 |
| 2.25 | 7.500 | 7.014 | 7.508 | 3.820 | −0.158 |
| 2.75 | 7.500 | 6.949 | 7.508 | 3.820 | −0.176 |
| 3.25 | 7.500 | 6.884 | 7.508 | 3.820 | −0.195 |
| 3.75 | 7.500 | 6.822 | 7.508 | 3.820 | −0.212 |
| 4.25 | 7.500 | 6.760 | 7.508 | 3.820 | −0.228 |
| 4.75 | 7.500 | 6.700 | 7.508 | 3.820 | −0.244 |

As used in Table 1, the column labeled Approximant Diopter Change refers to the projected diopter power change from the apex (center) of the lens to transition zone of the lens when implanted into the cornea. Whereas the center value would be +4.00 diopters the edge would have a value of 2.25 diopters less positive power. The lens anterior surface progressively changes from apex to edge. The table above is only a representative sample of diopter changes. For example, the diopter change for the corneal implant 10 may range from 0.12 diopter to 10 diopters for a given implant. The particular diopter for a corneal implant 10 will depend on a given patient' corrective needs.

The column labeled Posterior Radius refers to the back surface of the lens having contact with the stromal bed. The value for the Posterior Radius as used in Table 1 is measured in millimeters. Table 1 illustrates utilizing a posterior radius of 7.5 mm for each of the listed implants. The posterior radius may be varied depending on the particular posterior radius desired. In other embodiments, the posterior surface does not have a posterior radius of curvature, but is instead flat or has some other shaped surface or is textured.

The column labeled Anterior Apex Radius refers to the radius at the optical axis, or apex (center) in millimeters, needed to achieve desired corneal shape.

The column labeled Anterior End Radius refers to the target radius in millimeters at the end of the aspheric zone or outside diameter of said zone needed to achieve desired corneal shape.

The column labeled Anterior Semi-Diameter refers to the diameter of the desired aspheric zone measured in millimeters.

The column labeled Anterior Asphericity is the resultant Q value. In the examples shown in Table 1, the resultant Q value indicates that the anterior aspheric surface of the lens has a an aspheric ellipsoidal shape.

Figure 2:
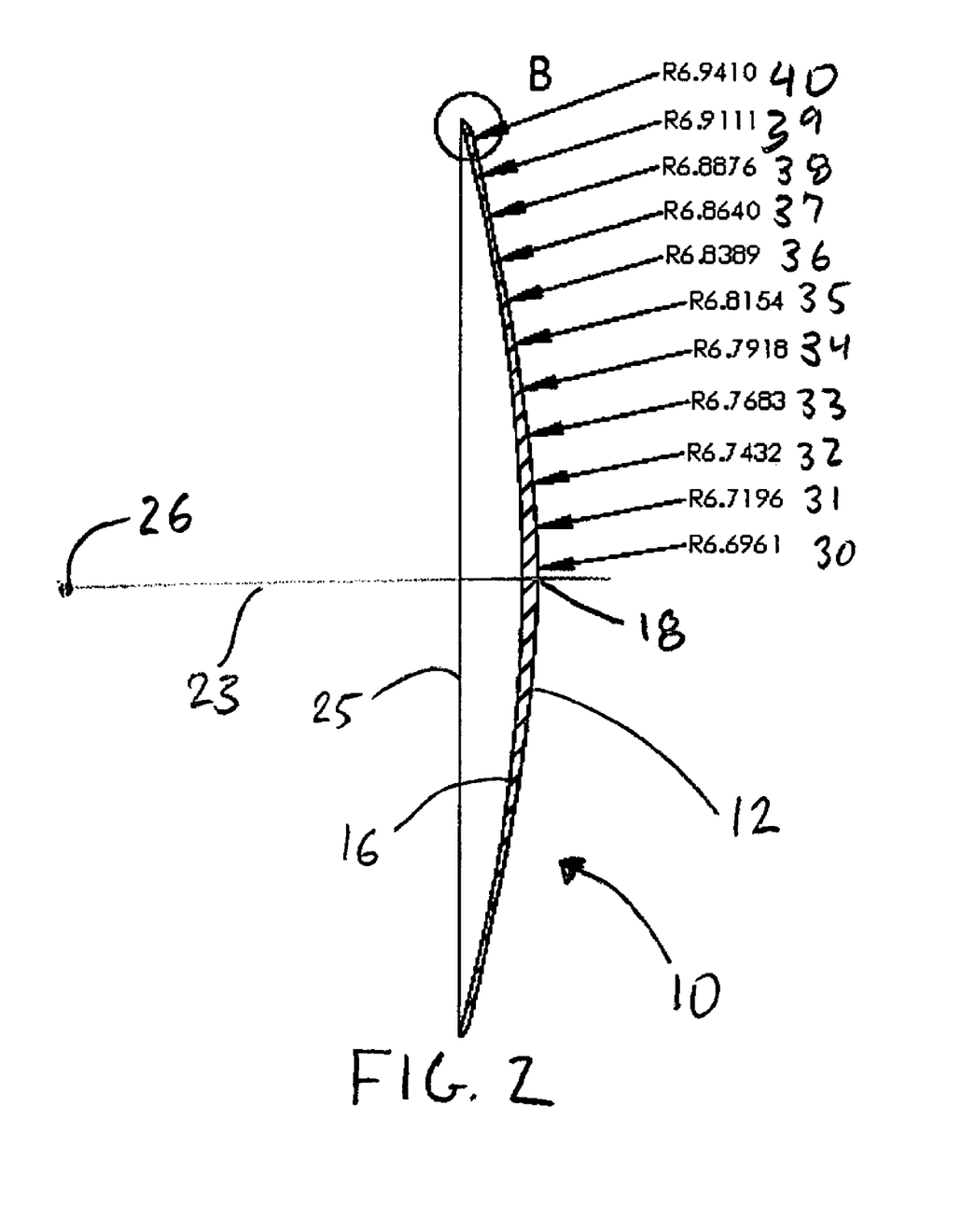
FIG. 2 is a cross-sectional view illustrating the nature of an aspherical continues surface.

Referring now to FIG. 2, an example of an aspheric surface is shown. Line 23 is perpendicular to line 25. Point 26 is on line 23 which passes through the apex of the implant 10. FIG. 2 is not drawn completely to scale, but nevertheless illustrates the nature of the aspheric surface. The radius from point 26 to the surface indicated by arrow 30 is a radius of 6.6961 mm. The radius from point 26 to the surface indicated by arrow 31 is a radius of 6.7196. The follow Table 2 shows the remaining indicated radii from point 26.

TABLE 2

| Arrow | Radii in mm |
|---|---|
| 32 | 6.7432 |
| 33 | 6.7683 |
| 34 | 6.7918 |
| 35 | 6.8154 |
| 36 | 6.8389 |
| 37 | 6.8640 |
| 38 | 6.8876 |
| 39 | 6.9111 |
| 40 | 6.9410 |

The particular points of the aspheric surface 12 show in FIG. 2 that the radii of curvature from point 26 increases from the apex 18 as the surface moves towards the outer edge of the implant. In a normal spherical surface, a lens would have a constant radii of curvature along the surface of the lens. As shown in FIG. 2, the inventive corneal implant 10 does not have a spherical surface, but instead a continuous aspheric surface from the apex of the implant.

The corneal implant 10 with the aspheric when implant is designed to reshape or re-contour the surface of the cornea by steepening or flattening the overall radius of curvature of the human cornea, while maintaining the correct natural aspheric surface.

In various embodiment, the corneal implant 10 with the aspheric surface can simultaneously correct the refractive error for distance vision (farsighted) and correct for near vision (reading). To achieve this, additional power is added to the central portion of the lens to correct the (reading add). For example, a patient with a refractive error of +3.00 diopters for distance, a positive 2 diopters is added to this needed distance correction for reading. This calculates to a starting diopter power at the apex of the corneal implant of +5.00 diopters which will progressively change to +3.00 diopters at the outer edge.

Taking the +5.00 diopters at apex the Q value can be calculated that is required to bring the lens surface (or cornea) from +5.00 diopters to +3.00 diopters within a designed lens diameter. An example would be to set the apex start at +5.00 and reduce the amount of aspheric change to within only 2.00 mm of the central portion of the lens. This result would then set this area of the lens to change progressively from +5.00 diopter to +4.50 diopters. From this point of 2.00 mm to 5.00 mm (remainder of lens) the asphericity can be set at a value to bring the remainder of the lens progressively from the +4.50 diopter to the required +3.00 diopter that the patient needed for distance correction. With this aspheric re-contouring using the inventive corneal implant 10, progressive change can be made which follow the natural shape of the human cornea.

The corneal implant 10 has a lens body formed of an optically clear bio-compatible material. In a preferred embodiment, the bio-compatible material has an index of refraction substantially similar to that of human corneal tissue (1.376). Thus, in a preferred embodiment, the refractive index of the implant material should be in the range of 1.36-1.39. Having such a refractive index prevents optical aberrations due to edge effects at the cornea-implant interface.

The corneal implant 10 is preferably made from a visually clear, permeable, microporous hydrogel with a water content greater than 40% up to approximately 90%. In other embodiments, the refractive index may be different from the refractive index of the corneal tissue. In such embodiments, in addition to the change in the shape of the cornea caused by the implantation of the lens, the actual material would have a refractive effect. Other embodiments from which the corneal implant may be made, include: polymethlmethacrylate (PMMA), silicone polymers, UV-absorbing acrylic, hydrogel, microporous hydrogel, collamer, collagel acrylic polymers, and other composite materials.

Figure 4A:
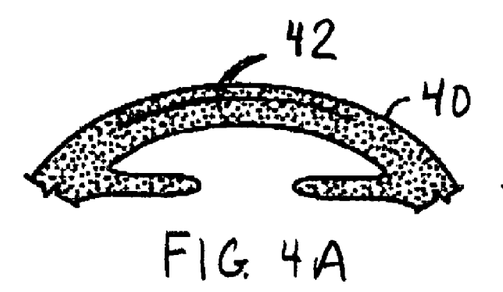
FIGS. 4A and 4B are schematic representations of a lamellar dissectomy, with FIG. 4B showing in particular the portion of the dissected cornea being connected through a hinge to the intact cornea.
Figure 4B:
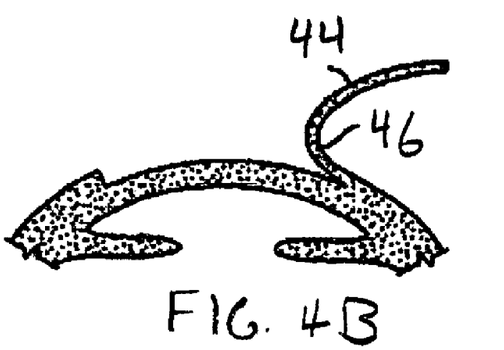

The present corneal implant 10 can be implanted in the cornea using a lamellar dissectomy shown schematically in FIGS. 4A, 4B. In this procedure, a keratome (not shown) is used in a known way to cut a portion of the outer surface of the cornea along line 42 as shown in FIG. 4A. This type of cut is used to form a corneal flap 44 shown in FIG. 4B, which remains attached to the cornea 40 through what is called a hinge 46. The hinge 46 is useful for allowing the flap 44 to be replaced with the same orientation as before the cut.

Figure 4C:
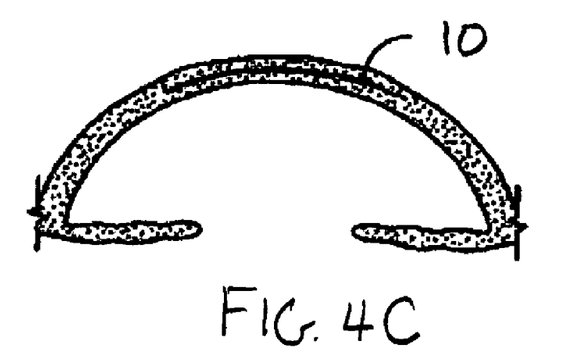
FIG. 4C is a schematic representations of a cornea in which the corneal implant have been implanted.

As is also known in the art, the flap is cut deeply enough to dissect the Bowman's membrane portion of the cornea, such as in keratome surgery or for subsequent moving of the tissue by laser or surgical removal. Other known techniques of cutting a flap in the cornea, such a utilizing a laser to create a flap or a pocket in which to place the implant, may also be used. A corneal flap of 100 to 200 microns, typically 160 to 200 microns, is made to eliminate the Bowman's membrane tension (which minimizes corneal nerve damage). This helps to conform the flap to the lens surface, thereby transferring all of the change of the shape to the anterior surface of the cornea. This makes refractive correction more reliable and predictable. Also, the possibility of extrusion of the implants is reduced due to pressure generated within the cornea caused by the addition of the implant. The corneal implant 10 is shown implanted in the cornea in FIG. 4C respectively, after the flap has been replaced in its normal position. These figures show the corrected shape for the outer surface of the cornea as a result of implants of the shapes described.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A corneal implant, comprising:
a lens body formed of an optically clear, bio-compatible material, the lens body having an anterior surface and a posterior surface, and an outer diameter edge;
the bio-compatible material having a refractive index ranging from 1.36-1.39; and
the anterior surface being convex in shape and being formed with a continuous aspheric surface,
wherein the lens body is adapted to be disposed posterior to a first portion of the cornea and anterior to a second portion of the cornea when implanted,
wherein the continuous aspheric surface is defined by the formula:
$X^2+Y^2+(1+Q)Z^2+2ZR=0$, wherein the Z axis is the optical axis of the implant, wherein the aspheric surface is a circularly symmetric surface about the Z axis with the apex of the surface at the coordinates $X=0, Y=0, Z=0$, wherein Z is the coordinate of the surface along the Z axis, wherein X and Y are the coordinates of the surface in the plane perpendicular to the Z axis, wherein R is the radius of curvature at the apex of the implant, and wherein Q is the surface asphericity of the aspheric surface and $Q<0$.

2. The implant of claim 1, wherein the posterior surface is concave in shape.

3. The implant of claim 2, wherein the posterior surface is curved in shape with a posterior radii of curvature.

4. The implant of claim 1, wherein the lens body has a thickness less than about 0.150 mm.

5. The implant of claim 1, wherein the lens body has a diameter between about 2.0 mm and about 7.0 mm.

6. The implant of claim 1, wherein the outer diameter edge has a thickness less than about 0.015 mm.

7. The implant of claim 1, wherein the outer diameter edge has a substantially planar surface.

8. The implant of claim 1, wherein the aspheric surface is adapted for the correction of presbyopia.

9. The implant of claim 1, wherein the aspheric surface is adapted for the correction of hyperopia.

10. The implant of claim 1, wherein the aspheric surface is adapted for the correction of myopia.

11. The implant of claim 1, wherein the lens body has a beveled surface connecting the outer diameter edge and the aspheric surface.

12. The implant of claim 11, wherein the beveled surface is substantially planar in a cross sectional side view of the lens body.

13. The implant of claim 11, wherein the anterior surface has an apex, and the continuous aspheric surface extends at least 1.0 mm radially outward from the apex.

14. The implant of claim 11, wherein the anterior surface has an apex, and the continuous aspheric surface extends from the apex to the beveled surface.

15. The implant of claim 1, wherein the lens body is circular in shape.

16. The implant of claim 1, wherein the optically clear, bio-compatible material is a permeable, microporous hydrogel.

17. The implant of claim 1, wherein then microporous hydrogel has a water content greater than 40% and up to approximately 90%.

18. A corneal implant, comprising:
a lens body formed of an optically clear, bio-compatible material, the lens body having an anterior surface with an apex and a posterior surface, and an outer diameter edge;
the bio-compatible material having a refractive index ranging from 1.36-1.39;
the anterior surface being convex in shape and being formed with a continuous aspheric surface,
wherein the lens body is adapted to be disposed posterior to a first portion of the cornea and anterior to a second portion of the cornea when implanted,
wherein every arc of the anterior surface extending from the apex to an outer edge of the anterior surface has a radius of curvature that varies along the entire length of the arc.

19. The implant of claim 18, wherein the lens body has a beveled surface connecting the outer diameter edge and the aspheric surface.

20. The implant of claim 18, wherein the posterior surface is concave in shape.

21. The implant of claim 20, wherein the posterior surface is curved in shape with a posterior radii of curvature.

22. The implant of claim 18, wherein the aspheric surface is adapted for the correction of presbyopia.

23. The implant of claim 18, wherein the aspheric surface is adapted for the correction of hyperopia.

24. The implant of claim 18, wherein the aspheric surface is adapted for the correction of myopia.

25. The implant of claim 19, wherein the beveled surface is substantially planar in a cross sectional side view of the lens body.

26. The implant of claim 19, wherein the continuous aspheric surface extends from the apex to the beveled surface.

27. The implant of claim 18, wherein the lens body is circular in shape.

28. The implant of claim 18, wherein the continuous aspheric surface extends at least 1.0 mm radially outward from the apex.

29. The implant of claim 18, wherein the optically, clear bio-compatible material is a permeable, microporous hydrogel.

30. The implant of claim 29, wherein then microporous hydrogel has a water content greater than 40% and up to approximately 90%.

31. The implant of claim 18, wherein the aspheric surface is defined by the formula: $X^2+Y^2+(1+Q)Z^2-2ZR=0$, wherein the Z axis is the optical axis of the implant, wherein the aspheric surface is a circularly symmetric surface about the Z axis with the apex of the surface at the coordinates $X=0, Y=0, Z=0$, wherein Z is the coordinate of the surface along the Z axis, wherein X and Y are the coordinates of the surface in the plane perpendicular to the Z axis, wherein R is the radius of curvature at the apex of the implant, and wherein Q is the surface asphericity of the aspheric surface and $Q<0$.

32. A corneal implant, comprising:
a lens body formed of an optically clear microporous hydrogel, the lens body having an anterior surface and a posterior surface, and an outer diameter edge, the outer diameter edge having a thickness less than about 0.015 mm, the lens body having a diameter between about 2.0 mm and 7.0 mm;
the bio-compatible material having a refractive index ranging from 1.36-1.39; and the anterior surface being convex in shape and being formed with a continuous aspheric surface,
wherein the lens body has a beveled surface connecting the outer diameter edge and the aspheric surface,
wherein the lens body is adapted to be disposed posterior to a first portion of the cornea and anterior to a second portion of the cornea when implanted,
wherein the aspheric surface is defined by the formula: $X^2+Y^2+(1+Q)Z^2-2ZR=0$, wherein the Z axis is the optical axis of the implant, wherein the aspheric surface is a circularly symmetric surface about the Z axis with the apex of the surface at the coordinates $X=0, Y=0, Z=0$, wherein Z is the coordinate of the surface along the Z axis, wherein X and Y are the coordinates of the surface in the plane perpendicular to the Z axis, wherein R is the radius of curvature at the apex of the implant, and wherein Q is the surface asphericity of the aspheric surface and $Q<0$.

33. The implant of claim 32, wherein the lens body is circular in shape.

34. The implant of claim 32, wherein the outer diameter edge has a substantially planar surface.

35. The implant of claim 32, wherein the aspheric surface is adapted for the correction of presbyopia.

36. The implant of claim 32, wherein the aspheric surface is adapted for the correction of hyperopia.

37. The implant of claim 32, wherein the aspheric surface is adapted for the correction of myopia.

38. The implant of claim 32, wherein the anterior surface has an apex, and the continuous aspheric surface extends from the apex to the beveled surface.

39. The implant of claim 32, wherein the lens body is circular in shape.

40. The implant of claim 32, wherein the anterior surface has an apex, and the continuous aspheric surface extends at least 1.0 mm radially outward from the apex.

41. The implant of claim 32, wherein then microporous hydrogel has a water content greater than 40% and up to approximately 90%.

42. A method of implanting a corneal implant, said method comprising the steps of:
(a) cutting away a portion of the outer surface of a cornea;
(b) implanting a lens on the exposed surface of the cornea, said lens having a lens body formed of an optically clear, bio-compatible material, the lens body having an anterior surface with an apex and a posterior surface, and an outer diameter edge, the bio-compatible material having a refractive index ranging from 1.36-1.39, and the anterior surface being convex in shape and being formed with a continuous aspheric surface,
wherein every arc of the anterior surface extending from the apex to an outer edge of the anterior surface has a radius of curvature that varies along the entire length of the arc; and
(c) replacing the portion of the cornea that was cut away.

43. The method of claim 42, wherein the posterior surface is concave in shape.

44. The method of claim 43, wherein the posterior surface is curved in shape with a posterior radii of curvature.

45. The method of claim 42, wherein the lens body has a thickness less than about 0.150 mm.

46. The method of claim 42, wherein the lens body has a diameter between about 2.0 mm and about 7.0 mm.

47. The method of claim 42, wherein the outer diameter edge has a thickness less than about 0.015 mm.

48. The method of claim 42, wherein the outer diameter edge has a substantially planar surface in a cross sectional side view of the lens body.

49. The method of claim 42, wherein the aspheric surface is adapted for the correction of presbyopia.

50. The method of claim 42, wherein the aspheric surface is adapted for the correction of hyperopia.

51. The method of claim 42, wherein the aspheric surface is adapted for the correction of myopia.

52. The method of claim 42, wherein the lens body has a beveled surface connecting the outer diameter edge and the aspheric surface.

53. The method of claim 52, wherein the anterior surface has an apex, and the continuous aspheric surface extends at least 1.0 mm radially outward from the apex.

54. The method of claim 52, wherein the anterior surface has an apex, and the continuous aspheric surface extends from the apex to the beveled surface.

55. The method of claim 42, wherein the lens body is circular in shape.

56. The method of claim 42, wherein the optically clear, bio-compatible material is a permeable, microporous hydrogel.

57. The method of claim 42, wherein then microporous hydrogel has a water content greater than 40% and up to approximately 90%.

58. The method of claim 42, wherein the aspheric surface is defined by the formula: $X^2+Y^2+(1+Q)Z^2-2ZR=0$, wherein the Z axis is the optical axis of the implant, wherein the aspheric surface is a circularly symmetric surface about the Z axis with the apex of the surface at the coordinates $X=0, Y=0, Z=0$, wherein Z is the coordinate of the surface along the Z axis, wherein X and Y are the coordinates of the surface in the plane perpendicular to the Z axis, wherein R is the radius of curvature at the apex of the implant, and wherein Q is the surface asphericity of the aspheric surface and $Q<0$.

* * * * *